(12) United States Patent
Alrumaih

(10) Patent No.: US 12,011,334 B2
(45) Date of Patent: *Jun. 18, 2024

(54) METHOD FOR TREATING A PATIENT WITH A TOOTH VACANCY

(71) Applicant: Imam Abdulrahman Bin Faisal University, Dammam (SA)

(72) Inventor: Hamad Saleh Hamad Alrumaih, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 297 days.

This patent is subject to a terminal disclaimer.

(21) Appl. No.: 17/699,634

(22) Filed: Mar. 21, 2022

(65) Prior Publication Data
US 2022/0202542 A1 Jun. 30, 2022

Related U.S. Application Data

(62) Division of application No. 16/373,139, filed on Apr. 2, 2019, now Pat. No. 11,324,574.

(51) Int. Cl.
*A61C 8/00* (2006.01)
*A61B 17/16* (2006.01)
(Continued)

(52) U.S. Cl.
CPC ........ *A61C 8/0092* (2013.01); *A61B 17/1688* (2013.01); *A61B 17/176* (2013.01); *A61B 17/1785* (2016.11); *A61B 17/24* (2013.01); *B33Y 50/00* (2014.12); *B33Y 80/00* (2014.12); *A61B 2017/00526* (2013.01); *A61B 2017/00743* (2013.01); *A61B 2017/00831* (2013.01); *A61B 17/1615* (2013.01); *A61B 2017/568* (2013.01); *A61B 2034/105* (2016.02); *A61B 2034/108* (2016.02); *A61C 1/084* (2013.01); *A61F 2/186* (2013.01); *A61F 2/4644* (2013.01)

(58) Field of Classification Search
CPC ......... A61C 8/88; A61C 8/0092; A61B 17/17; A61B 17/176; A61B 17/1785; A61B 17/24; A61B 17/16; B33Y 50/00; B33Y 80/00
See application file for complete search history.

(56) References Cited

U.S. PATENT DOCUMENTS 11,324,574 B2 * 5/2022 Alrumaih ............. A61C 8/0092
2005/0021142 A1   1/2005 Ganz et al.
(Continued)

FOREIGN PATENT DOCUMENTS

CN    105982747 A    10/2016
CN    107224335 A    10/2017

OTHER PUBLICATIONS

M. Vehmeijer, et al., "A Novel Method of Orbital Floor Reconstruction Using Virtual Planning, 3-Dimensional Printing, and Autologous Bone" Journal of Oral and Maxillofacial Surgery, Mar. 2016, pp. 1-6.

(Continued)

*Primary Examiner* — Christopher J Beccia
(74) *Attorney, Agent, or Firm* — Oblon, McClelland, Maier & Neustadt, L.L.P.

(57) ABSTRACT

An accurate and precise surgical guide for dental procedures, especially a procedure involving a subject with few or no teeth as well as methods for making and use of such guides.

10 Claims, 4 Drawing Sheets

Figure 1:
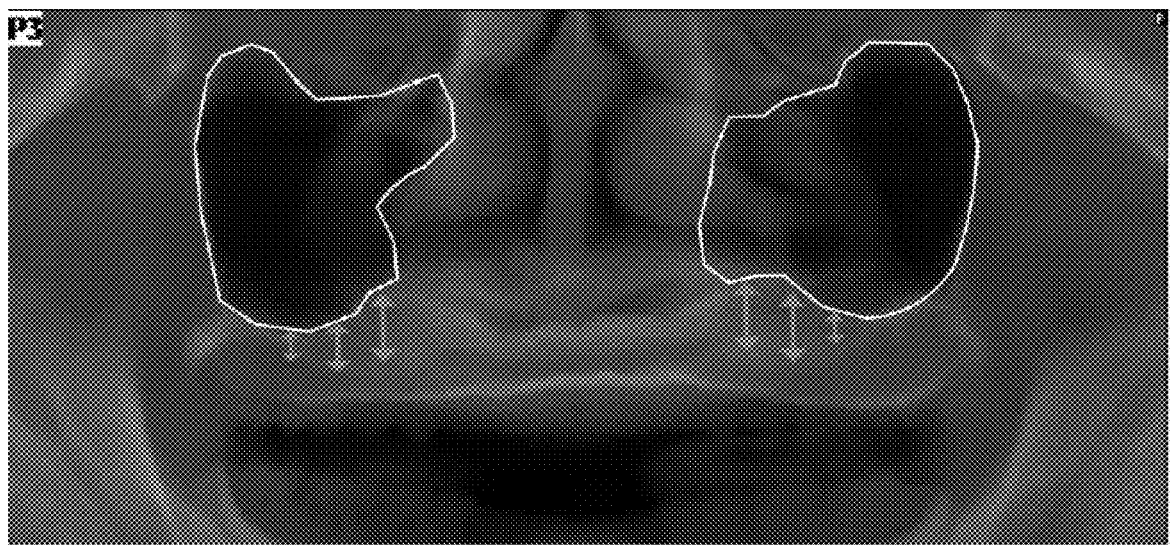

(51) Int. Cl.
    *A61B 17/17*     (2006.01)
    *A61B 17/24*     (2006.01)
    *B33Y 50/00*     (2015.01)
    *B33Y 80/00*     (2015.01)
    *A61B 17/00*     (2006.01)
    *A61B 17/56*     (2006.01)
    *A61B 34/10*     (2016.01)
    *A61C 1/08*     (2006.01)
    *A61F 2/18*     (2006.01)
    *A61F 2/46*     (2006.01)

(56) References Cited

U.S. PATENT DOCUMENTS

2010/0191242 A1*   7/2010   Massoud .............. A61B 17/176
                                                                                606/87
2016/0374784 A1*  12/2016   Joshi .................... A61C 9/0053
                                                                                 433/214
2020/0160497 A1*   5/2020   Shah ....................... G06T 7/001

OTHER PUBLICATIONS

B. Goodacre, et al., "A 3D-printed guide for lateral approach sinus grafting: A dental technique" Journal of Prosthetic Dentistry, vol. 119, Issue 6, Jun. 2018, pp. 897-901.

* cited by examiner

METHOD FOR TREATING A PATIENT WITH A TOOTH VACANCY

CROSS-REFERENCE TO RELATED APPLICATIONS

The present application is a Divisional of U.S. application Ser. No. 16/373,139, now allowed, having a filing date of Apr. 2, 2019.

BACKGROUND OF THE INVENTION

Field of the Invention

The invention relates to a surgical guide for use in the fields of dental surgery and prosthetics. More specifically the invention relates to a surgical guide for edentulous patients to be used in maxillary surgical procedures such as sinus elevation or grafting in preparation for installation of dental or endosseous implants which form intimate bonds to bone. These implants in turn support dental prosthesis such as a crown, bridge, denture, facial prosthesis or act as orthodontic anchors.

Description of Related Art

The "background" description provided herein is for the purpose of generally presenting the context of the disclosure. Work of the presently named inventor to the extent it is described in this background section as well as aspects of the description which may not otherwise qualify as prior art at the time of filing, are neither expressly or impliedly admitted as prior art against the present invention.

Following maxillary posterior tooth loss, the maxillary sinus expands in every dimension towards the maxilla. As maxillary bone resorbs, the sinus is enlarged in a coronal, lateral, anterior and posterior direction. This expansion of the maxillary sinus resulting from maxillary bone resorption leaves less maxillary bone for a platform on which to place dental implants. If too much maxillary bone has been resorbed, then placement of a dental implant can penetrate the floor of the sinus leaving the apical portion of the implant exposed in the sinus and not engaged in bone. This results in a lack of bony support around that portion of the implant and frustrates the purpose of stably anchoring dental implants in the maxilla.

In preparation for dental implant placement in the posterior maxilla, a clinician must evaluate the position of the maxillary sinus relative to the remaining maxillary bone and determine whether bone resorption has occurred to the point of leaving insufficient bone mass for implant placement. When it is determined that insufficient bone mass exists for placement of dental implants, then additional surgical procedures, such as sinus elevation and grafting, are required prior to implant placement to provide an adequate foundation in maxillary bone for the implants.

A prevalent method of sinus elevation and grafting is called the Caldwell-Luc Osteotomy. However, historically, Caldwell-Luc technique and other techniques for sinus approaches did not mention guides to be used during a surgical procedure. The procedure involves reflecting a full thickness mucosal flap to expose the lateral wall of the sinus and maxilla. A lateral osteotomy is then prepared in the lateral wall of the maxillary sinus. The osteotomy is rectangular in shape and is cut as deep as the lateral wall of the maxillary sinus until the sinus membrane (Schneiderian membrane) is exposed. The window, or osteotomy, is then carefully tapped medially to allow entry into the sinus cavity. Afterwards, the sinus membrane is gently elevated from the floor and the anterior and posterior walls of the sinus utilizing various blunt dissecting instruments. After the sinus membrane has been elevated and retracted apically and medially, bone is then placed in the area from which the sinus membrane has been elevated. The mucosal flaps are then approximated and sutured.

One of the technical difficulties encountered during this procedure is the inability of the operator to precisely locate the floor of the sinus while preparing the osteotomy from an antero-posterior direction (along the X-Y axis). Since the floor of the sinus can elevate and descend variably as the osteotomy moves antero-posteriorly, it is impossible to visualize this course. Therefore, the osteotomy is generally prepared in a straight line higher than the highest point of the sinus floor. This guarantees penetration into the sinus floor since an osteotomy that is lower than the sinus floor at any point will simply penetrate into the maxillary bone and not into the sinus cavity. This would require adjustment by expanding the osteotomy superiorly (apically) in order to penetrate the sinus cavity. The additional trimming of bone is traumatic and unnecessarily removes bone.

Another error occurs if the osteotomy is placed too superior to the floor of the sinus. Careful manipulation must then be effected in order to negotiate the remaining lateral wall of the sinus inferior to the osteotomy and to descend below the Schneiderian membrane in order to elevate it from the sinus floor. This technically difficult maneuvering of the instruments along two planes increases the risk of tearing the membrane and thus compromising the outcome of the graft. Otherwise, the osteotomy must be adjusted by expanding in an inferior direction. This would lead to additional trimming of bone and increase the risk of tearing the membrane during the expansion of the osteotomy. It is nearly impossible to visualize the variable course of the sinus floor as the osteotomy progresses antero-posteriorly. This inability to visualize the course of the sinus floor is the first difficulty encountered in the procedure.

Another difficulty encountered is the varying thickness of the lateral wall of the sinus as the osteotomy penetrates it to expose the underlying Schneiderian membrane. The operator must penetrate fully through the lateral wall (X-Z axis) in order to raise the window and elevate the membrane. However, if the osteotomy is prepared too deep, it can tear through the fragile membrane. Therefore, great operator skill is required to visualize the membrane as the osteotomy is prepared through a varying depth of the lateral wall and the membrane is approached.

A further difficulty encountered is the anterior wall of the sinus. Besides the varying depth of the lateral wall, the anterior wall can also vary in course in the Y-X axis just as the floor can vary in course in the X-Y axis and the lateral wall can vary in thickness in the Y-Z axis. Since the osteotomy is usually placed in a straight line apico-coronally (vertically), whereas the anterior wall is usually not a straight line, portions of the osteotomy would be too far posterior to the anterior wall. This would require manipulation anteriorly and then laterally to dissect the membrane from the lateral and anterior walls thus increasing the risk of tearing the membrane from the difficult manipulation in two planes. Again, any additional adjustments to the osteotomy would cause unnecessary bone removal and trauma as well as increase the risk of tearing the membrane.

This technique significantly relies on careful approximation of an outline of the area of the sinus to be grafted so that a planned osteotomy will be inside the sinus borders for a successful procedure. During an actual osteotomy, it is nearly impossible to accurately follow the varying course of the sinus. Inevitably there are areas that are not exposed by the osteotomy which require careful manipulation of the sinus membrane and risk damage to the membrane. Additionally, the lateral wall of the sinus has a variable thickness, so as it is being cut the surgeon must proceed very carefully and rely on visual as well as tactile senses to establish that the wall has been pierced without entering the sinus so as to not damage the immediately underlying membrane.

To more reliably reveal the dimensions of the maxillary sinus and related structures, the maxillary sinus can be graphed in three dimensions through a computerized axial tomography (CAT or CT) scan that renders the sinus in the X, Y and Z planes. The CT scan can then be formatted for evaluation utilizing three-dimensional (3-D) imaging software. The 3-D imaging software allows the clinician to view the sinus in all dimensions as well as to manipulate the image and prepare a treatment plan as to the location and amount of bone to be grafted in the sinus in order to augment the missing maxillary bone that the sinus has expanded into. This information can then be utilized by the surgeon to establish the parameters of outline and volume of the area of the sinus to be entered for bone grafting.

Nevertheless, even with the information provided by the CT scan utilizing the 3-D imaging software as to the outline of the sinus in the X, Y and Z planes and all other parameters, there has been no mechanism to accurately transfer this highly precise information to the surgical field for its practical application. Meticulous planning of the parameters of the sinus to be elevated and augmented has been thwarted by the inaccurate approximation in the transfer of this information during the surgical procedure as well as inexact fabrication of surgical guides designed using this information.

Surgical guides are used during surgical dental procedures to position bone grafts and dental implants. These guides help a surgeon identify or avoid areas having poor bone quality, such as portions of the maxilla which have undergone resorption, as well as hidden anatomical features such as sinus cavities, nerves and vasculature.

Conventional surgical guides can be made by performing computerized axial tomograph (CAT or CT) scans and formatting the results for inspection using 3D imaging software.

However, there remains a significant need to more precisely transfer this information into a form useful during surgery, such as into an accurate surgical guide that allows a surgeon to avoid or select particular areas of the maxilla for surgical work. This need is particularly acute for edentulous patients who have lost teeth and for whom there are insufficient or unreliable anatomical reference points for bone grafting or other surgical procedures.

Existing procedures proposed for making surgical guides, such as those described by Massoud, US 2010/0191242, can lack precision in the ways they produce a surgical guide, for example, the surgical guides are produced by methods that involve use of plastics that require heat curing such as heat-cure acrylic resin or which cause shrinkage in a final produced surgical guide and thus introduce inaccuracy into the guide compared to the extremely precise imaging information used to design the guide. These deformations and distortions of the original imaging information affect the accuracy of a surgical procedure using the guide.

Due to the anatomical features of the maxilla and surrounding sites, even small distortions in a conventional surgical guide can produce rocking and ill-fitting guides which lack accuracy and can dramatically affect the X, Y and Z locations identifying a surgical procedure site, such as sites for sinus window preparation sites for dental implants. This lack of accuracy can displace the desired site of surgery identified by a medical scan to an inappropriate site having insufficient grafting materials or support. Thus such distortions can lead to the need for additional corrective surgery. Moreover, the lack of surgical guide precision can also cause irreversible injury to vital structures such as the maxillary artery or inferior alveolar nerve and increase patient discomfort and pain by irritating the adjacent teeth and gums.

Problems associated with proposed surgical guides are aggravated for edentulous patients or patients who have lost teeth. Often these patients experience significant resorption of facial bone along with loss of teeth. These patients already have an increased risk of insufficient bone material to support implants and can require more intensive surgical grafting procedures. Tooth loss can occur by tooth decay or due to periodontal disease. Poor bone quality in these patients as well as hidden features such as sinus cavities, nerves and nerve roots complicate dental implant procedures.

3D printing has been used to produce a printed mold for making an autologous bone graft for reconstruction of the orbital floor; see Vehmeijer, et al., Journal of Oral and Maxillofacial Surgery•March 2016 (DOI:10.1016/j.joms.2016.03.044 who use a printing process that deposits a layer of powder over which a printing head moves, depositing a binder that solidifies the powder. Stereolithography is a form of 3D printing technology used for creating models, prototypes, patterns, and production parts in a layer by layer fashion using photopolymerization, a process by which light causes chains of molecules to link, forming polymers. Those polymers then make up the body of a three-dimensional solid; https://_en.wikipedia.org/wiki/Stereolithography (last accessed Feb. 12, 2019, incorporated by reference).

A variety of different UV-curable resins is known, however, a primary limitation of their use is the limited light penetration depth which usually does not exceed a few millimeters. Typical UV-curable resins can contain oligomers, monomers (diluents), photo-polymerization initiator, coinitiators (e.g., spectral sensitizers or reducing agents), and various other additives such as stabilizers, antioxidants, plasticizers and pigments. The most versatile curing systems are free radical curing compositions. However, these are subject to oxygen inhibition where oxygen in air can stop surface molecules from polymerizing leaving a tacky layer.

A large number of acrylic-functionalized oligomers are commercially available including polyester and epoxy resins, aliphatic and aromatic urethanes, silicones and polyethers.

Besides free-radical curing systems, cationic systems based on epoxy and/or vinyl ether compounds are employed. However, only a limited number of monomers and oligomers are available for light induced cationic cure. Thus, the versatility in tailoring properties is rather limited. Furthermore, the photoinitiators used in cationic cure can be toxic and corrosive and cationic systems not subjected to air inhibition are easily poisoned by moisture in the air.

The inventors have recognized that polymerization shrinkage does not substantially occur with 3D printing and that this feature of 3D printing can advantageously be applied to producing a dental surgical guide. The invention provides a convenient way to provide an accurately fitting guide compared to other conventional methods subjects to polymerization shrinkage.

In view of the problems with existing production methods and the surgical guides they produce, a new method for producing highly accurate and precise surgical guides is needed. Consequently, the inventors sought to develop a surgical guide that increases the precision of bone grafting such as that performed prior to installation of dental implants, especially for edentulous patients.

BRIEF SUMMARY OF THE INVENTION

The invention disclosed herein is a surgical guide which is produced by 3D printing and is based on the treatment plan set forth from the diagnostic information provided by 3-D imaging software from a CT scan taken of a patient. The surgical guide is custom shaped and dimensioned based on the CT scan and 3-D imaging software results of the sinus area for each patient. This permits a surgeon to accurately prepare an osteotomy, such as a Caldwell-Luc osteotomy, in all three planes. The outline of the osteotomy, as well as the depth of the bone to be removed without damaging the underlying the Schneiderian Membrane is created utilizing the surgical guide in conjunction with a proper depth bur permitting open access to the maxillary sinus cavity within the dimensions required for a sinus elevation. It provides a surgeon easy access to the Schneiderian Membrane without anatomical obstructions.

Prior surgical procedures were performed using only an approximation as to where the floor of the sinus was, where the superior portion was, as well as where the anterior wall and the posterior wall were located. Moreover, the variable depth of the lateral wall of the sinus was accessed only with the experience and visual sense of the clinician who was not informed by exact measurements as to the varying thickness of the osteotomy as it moved along the x-y axis.

The surgical guide disclosed herein eliminates the need for approximations of the osteotomy in the x-y axis as to the outline of the osteotomy, as well as along the Z axis as to the depth of the osteotomy so as to prevent any damage of overcutting into the Schneiderian Membrane, thus enabling easy access into the sinus cavity as outlined by the treatment plan set forth utilizing 3-D imaging software from a CT scan of the patient's maxillary sinus.

Figure 2:
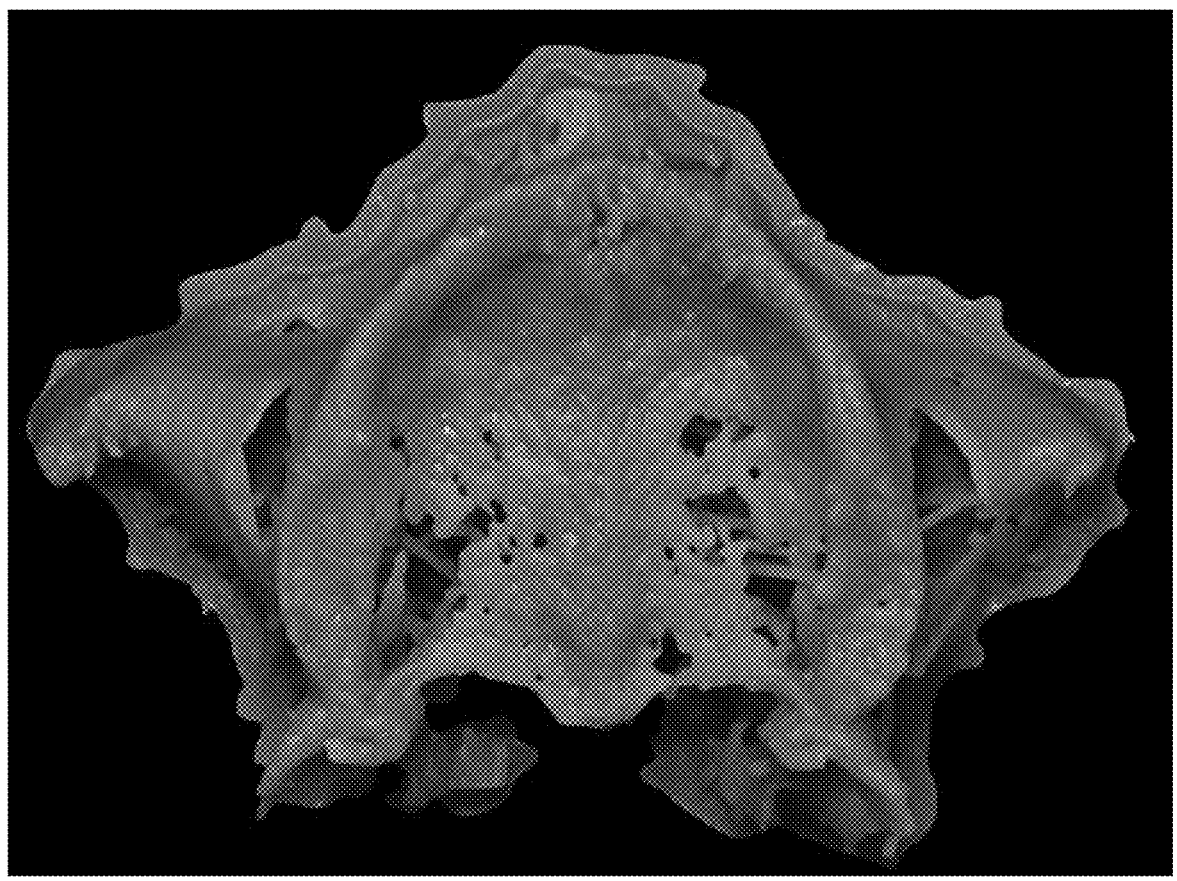
Figure 3:

One aspect of the invention is a method for making a maxillary sinus guide that includes performing cone beam computerized tomography ("CBCT") on a portion of the face comprising maxillary sinuses; preparing a digital imaging file from the results of the CBCT; exporting the digital imaging file to a 3D printer; printing a 3D model of the maxillary jaw of the patient as shown for example by FIG. 2; configuring a virtual bone-supported maxillary sinus guide to the printed 3D model of the maxillary jaw; producing a stereolithography file ("STL") of the virtual bone-supported maxillary sinus guide; exporting the STL file to a 3D printer; and printing the bone-supported maxillary sinus guide on the 3D printer as shown for example in FIG. 3.

This method may be used for any patient in need of dental surgery involving the maxilla and is especially advantageous for use with patents who have at least a partially resorbed maxilla, have lost one or more teeth, or who are edentulous.

The CBCT is preferably performed on a portion of the face encompassing at least a portion of the maxilla and preferably on both the face and jaw of the patient (FIG. 1). The results of the CBCT are transferred or stored on one or more digital imaging files, such as a Digital Imaging and Communications in Medicine ("DICOM") file (FIG. 2).

3D design or 3D engineering software, such as GEO-MAGIC® (https://_www.3dsystems.com/software) or other 3D engineering software to produce a StereoLithograph ("STL") file (https://_en.wikipedia.org/wiki/Stereolithography) of a bone-supported surgical guide. This design is based on data describing the maxilla obtained from a CBCT scan.

A 3D printer is used to produce a model guide to assess proper fit and positioning with respect to the maxilla or a final guide for use in a surgical procedure (FIG. 3). The guide may be produced from a suitable 3D printing material, preferably from an FDA approved material. Once printed, the alignment of the guide with the maxillary jaw of the patient may be tested, for example, by fitting it to a physical model of a patient's maxilla (FIG. 4), to a patients jaw (FIG. 5), or otherwise assessing its alignment. Preferably, a dental practitioner will perform a trial fitting of the 3D printed guide as this requires no surgical intervention and it only takes few minutes to check the fit. Such a trial fitting permits assessment of important metrics of a good fit including the lack of rocking and a passive seating. However, if minor rocking of tightness is detected during a trial fitting a material such as Fit Checker™ (e.g. a vinyl polyether silicone or functional equivalent) is used to determine the area of bad fit and a modification can be done using simple instruments. If significant rocking is observed or if the guide does not seat properly, then the guide may be redesigned as described herein and then test fit again.

With bone supported guides it is generally impractical to surgically expose the bone and perform a test fitting as this would require a substantial healing time such as 2 to 3 months prior to actually using the guide.

Misalignments of the printed 3D model of the guide may be visually detected by a practitioner or detected electronically or mechanically. A corrected virtual model of the bone-supported maxillary sinus guide is then made to more closely conform to the jaw of the patient, followed by producing a modified stereo lithography file ("STL") of the modified virtual bone-supported maxillary sinus guide, exporting the modified STL file to a 3D printer, and printing the modified bone-supported maxillary sinus guide on the 3D printer.

The guide produced by this method may be fitted, positioned or otherwise installed adjacent to the maxilla during a surgical procedure as a surgical guide (FIGS. 5 and 6), such as a dental procedure on an edentulous patient or a patient who has lost teeth or whose maxilla has been partially resorbed.

In some embodiments, a kit comprising a surgical guide for the left or right parts of the maxilla, surgical guides for both the left and right of the maxilla, surgical tools, such as surgical burrs, for use along with the surgical guide, dental implants, anesthetics, antiseptics, dental cements, and/or instructions for use may be assembled.

Another aspect of the invention is a 3D printed maxillary sinus guide produced by the methods disclosed herein. The surgical guide is produced by 3D printing using a 3D printing material or ink, preferably an FDA approved material. Advantageously, the 3D printed maxillary sinus guide is produced for an edentulous patient, a patient in need of sinus augmentation; or a patient in need of a dental implant. The surgical guide more precisely fits or aligns with the jaw of the patient than an otherwise identical sinus guide that was not produced by 3D printing, for example, from a material that is cured by heating.

Figure 5:

Additional aspects of the invention include surgical methods using the 3D printed guide as disclosed herein. These include a method for treating an edentulous or patient missing one or more teeth that involves placing the 3D printed bone supported sinus guide produced by the method disclosed herein in the mouth of the patient thereby marking access to the sinus. The surgical guide may be used for a procedure that requires surgically forming a lateral sinus window. During a surgical procedure the guide is used to view and position one or more surgical instrument, for example, during a sinus lift, sinus augmentation, or dental implantation. (https://_en.wikipedia.org/wiki/Sinus lift). During a surgical procedure, after opening of the surgical site by raising a tissue flap, the guide fits on the bone for only a few minutes while a medical pencil is used to mark of outline the surgical window as shown by FIG. 5. After that, the guide is removed.

Other specific, nonlimiting embodiments of the invention include the following.

A method for making a bone-supported maxillary sinus guide for an edentulous patient which includes obtaining an STL file describing a patient's maxillary bone structure as imaged by cone beam computerized tomography ("CBCT"); producing an STL file describing a bone-supported maxillary sinus surgical guide using implant planning software and the STL file describing the patient's maxillary bone structure, and 3D printing a bone-supported maxillary sinus surgical guide from a UV curable resin using the STL file describing a bone-supported maxillary sinus surgical guide, and curing the UV curable resin with light. This method may be performed with a dental resin of choice, preferably a resin that is cured by UV or blue light and which does not require heat curing. The resin may be an FDE recognized, tracked or approved resin for dental procedures.

In some embodiments, the method will involve obtaining a STL file describing the patient's maxillary bone structure comprises transforming data in a digital imaging and communications in medicine (DICOM) file into an STL file using DICOM reconstruction software. In some embodiments, the method described herein will further comprise of taking one or more CBCT scans to obtain the STL file(s) describing the patient's maxillary bone structure. It is not necessary to obtain a soft tissue or intraoral scan, though other types of scans may be performed in some embodiments.

The producing of an STL file describing a bone-supported maxillary sinus surgical guide may include determining a tooth implant position and/or determining a position of a window that covers a lateral wall of the sinus and zygomatic process of the maxilla. The producing an STL file describing a bone-supported maxillary sinus surgical guide further can include further contouring and/or smooth the design of the surgical guide.

In some embodiments 3D printing a bone-supported maxillary sinus surgical guide includes printing a prototype surgical guide, printing a scale model that includes maxillary surfaces in contact with the guide, and test fitting the guide to the model of the maxilla and/or to the patient's maxilla, and adjust the design of the surgical guide to more closely fit the model or patient's maxilla, and reprinting a more close-fitting surgical guide.

Another aspect of the invention is directed to dental surgery using a surgical guide as described herein. The guide is generally used for appropriate dental procedures where maxillary bone is built up or restored including a sinus lift or a sinus augmentation. In many procedures, the dental guide will be used to provide a solid foundation in bone for one or more dental implants.

The invention also pertains to the 3D printed surgical guide disclosed herein per se. This may be prepared using a UV cured FDA approved acrylic 3D printing material. In preferred embodiments, the 3D printed maxillary sinus guide as disclosed herein will more precisely fits or aligns with the jaw of the patient or with a 3D printed model of the jaw than an otherwise identical sinus guide that was not produced by 3D printing with a UV curable resin.

Other related embodiments are directed to a method for treating an edentulous or patient missing one or more teeth comprising placing a 3D printed bone supported sinus guide as disclosed herein in the mouth or directly in contact with the maxilla of the patient thereby marking access to the sinus. In some embodiments this method further includes surgically forming a lateral sinus window using the sinus guide; performing a sinus lift or sinus augmentation using the sinus guide; and/or installing a dental implant.

BRIEF DESCRIPTION OF THE SEVERAL VIEWS OF THE DRAWING(S)

FIG. 1. Cone Beam Computerized Tomography (CBCT) for edentulous patient to locate the sinuses and evaluate the remaining bone quality and quantity.

FIG. 2. Example of export of a DICOM file of patient CBCT to the 3D printer to print a 3D bone model for the maxillary jaw.

FIG. 3. Example of an export Stereo lithography (STL) file to the 3D printer to print a 3D bone supported sinus guide.

Figure 4:
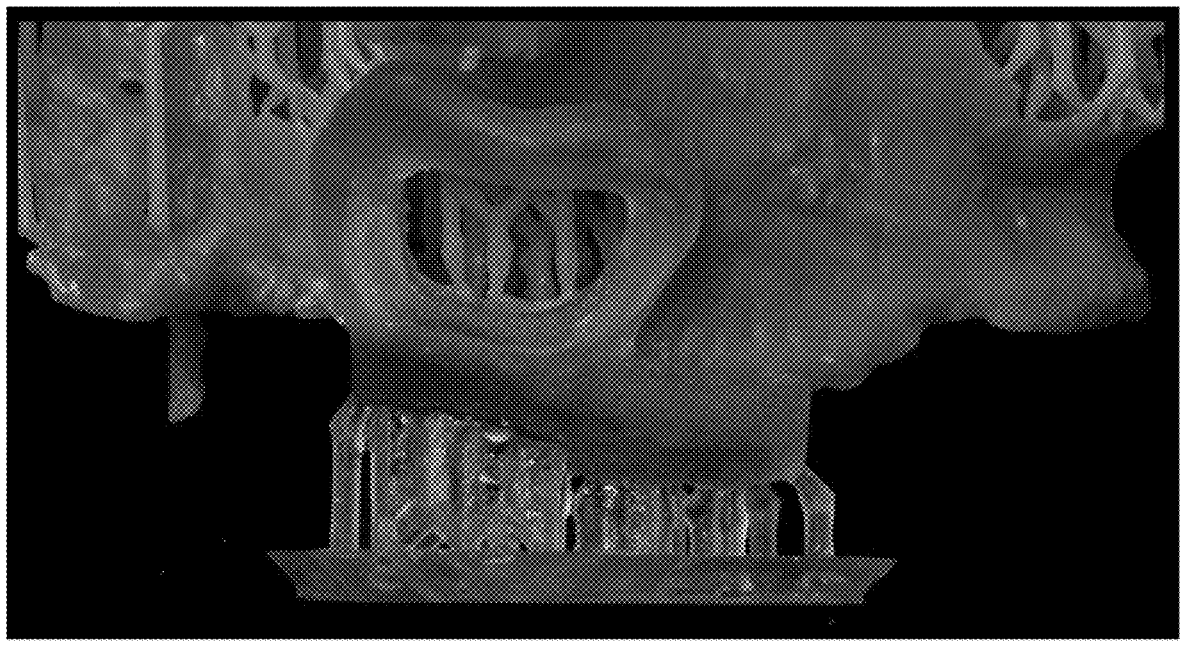

FIG. 4. Try-in procedure of a 3D bone-supported sinus guide on a bone model.

FIG. 5. Placement of a 3D printed sinus guide in a patient mouth marking lateral window entrance of sinus structure.

Figure 6:
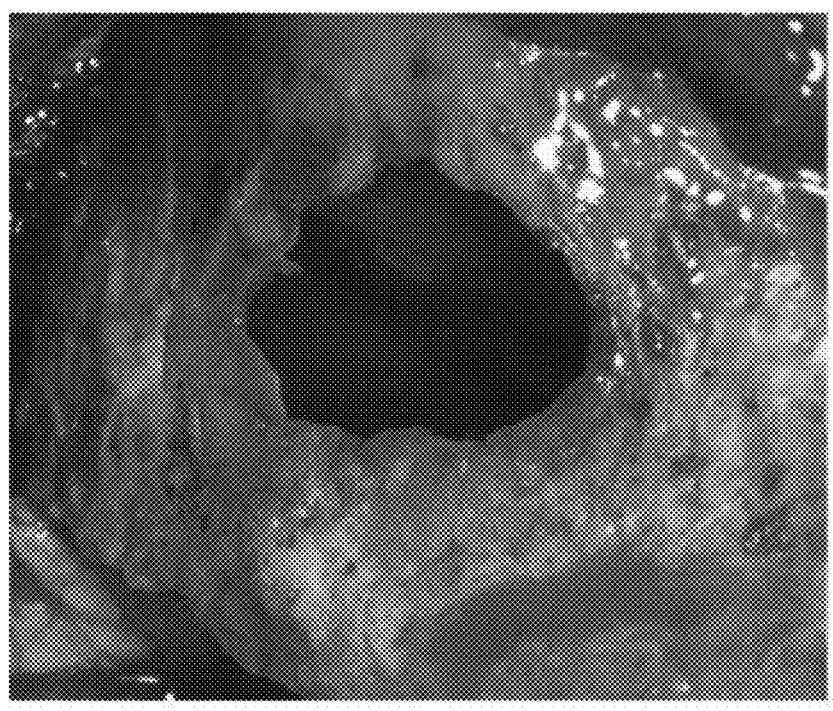

FIG. 6. Sinus lateral window attained by use of 3D printed surgical guide.

DETAILED DESCRIPTION OF THE INVENTION

Many materials are available to construct surgical guides, but past selections of materials have produced surgical guides that are unstable or which cannot be accurately positioned during surgery, such as guides that rock or which are ill fitting. Surprisingly, the inventors found use of 3D printing in combination with use of a 3D printing acrylic material that is not cured by heating can provide a superior guide that fits better, does not rock and thus is safer than conventional surgical guides especially for procedures for edentulous patients where a tooth supported guide is not feasible.

The term "bone supported" as used herein describes a surgical guide that is supported by the bone of the maxilla, such as a guide that fits over the gum covering the maxilla in an edentulous patient. A completely edentulous patient has no maxillary teeth to support a sinus guide and partially edentulous patients may not have teeth positioned so that they could support a sinus guide. Conventional sinus guides which are anchored to teeth position a surgical window based on the positions of the surrounding teeth, see for example, Goodacre, et al., J. of Prosthetic Dentistry (2018), "A 3D-printed guide for lateral approach sinus grafting: a dental technique" incorporated by reference. This is not possible for completely edentulous patients and not feasible for many partially edentulous patients.

The bone supported guide fits only on bone. After opening the flap surgically (gums incision and rising), the guide will be supported by exposed bone. So, the gum tissue is intervening in all times.

In contrast to conventional heat-curing methods, the inventors employ an acrylic material for 3D printing by stereolithography (SLA) that uses UV laser to cure liquid resin into hard plastic and does not require or include any heat process during making the guide. Stereo Lithography Apparatus (SLA) 3D printing uses a UV-sensitive liquid resin as the working material. A UV-laser is projected on and moves across the reservoir of the resin build material, illuminating and hardening the liquid resin only in the areas where the part is being printed. If multiple parts are being printed, each part is traced on the resin by the laser. The platform holding the part or parts lowers after each layer is printed, and a wiper blade spreads more build material uniformly across the working space. The UV laser makes another pass, tracing the outline of the next layer for each part in the print job. The process is repeated layer by layer until the job is complete. SLA technology allows for varying the layer thickness throughout the printing process. Some layers can be 100 µm thick where accuracy is not critical and then dialed to 50 µm or less when greater accuracy is required. SLA printing technology is available with a wide variety of materials. A 25-µm to 50-µm layer thickness is achievable with excellent accuracy and good surface finish. SLA typically has slower build times due to the laser outline of each part. Post-print processing may require cutting the final part from the support material, removal of excess material, and the parts placed in a UV oven for final curing.

The wavelength of UV light or near-UV ranges from about 10, 20, 50, 100, 200, 300, 400 to about 420 nm, preferably a UV curable resin is curable at a wavelength ranging from 200 to 420 nm. In some embodiments blue light having a wavelength ranging from about 400 to 500 nm may be used to cure a resin. These ranges include all intermediate subranges and values.

The invention provides a method for producing a surgical guide that is highly accurate compared to conventional guides. The guide is produced by a safe, user-friendly, and minimally invasive process. The method is fast and efficient and reduces the time needed to produce a surgical guide compared to conventional procedures and reduces the time a patient and surgeon must wait to complete the surgery.

The method of the invention is also useful for producing models or prototypes useful as educational tools between a patient and clinician or between patient, attending faculty and dental students. Acquisition of 3D data for design and construction of the device may use conventional procedures such as those described by Massoud, US 2010/0191242 (incorporated by reference, however, preferably CBCT is used to acquire data on the shape of a patient's maxilla and surrounding features. The 3D data from a CBCT scan may be transferred to software such as Geomagic® software which can be used to design a surgical guide conforming to or positioned over the appropriate parts of the maxilla described by the CBCT scan.

Data describing the surgical guide as well as the maxilla as described by the CBCT scan is then incorporated into an STL file and sent to a 3D printer in which a select FDA tracked/approved 3D printer ink is used such as an FDA approved acrylic material. Only a short time is required for printing the guide, for example, about 10, 15, 20, 25 or 30 minutes at a materials cost of less than $10.00.

Once printed, the surgical guide can be physically imposed, positioned, on or tried on the 3D printed maxilla from the CBCT scan. Further refinements may be made to the design of the surgical guide based on the results of the matching the 3D-printed surgical guide to the 3D-printed maxilla. Once a practitioner is satisfied with the fit and design of the 3D-printed surgical guide, it may be sterilized, placed inside the patient's mouth and used to define a lateral window in the maxilla.

Prior methods which cast or produce a guide from acrylic resin but do not use 3D printing introduce inaccuracy into a surgical guide because dimensional changes due to the exothermal heat during conventional processing which can significantly alter lateral window outline. In contrast, 3D printing technology has no dimensional changes which leads to higher accuracy and precision.

The surgical guide and method disclosed herein permits a surgeon to visually evaluate the anatomical structure a patient's maxilla which can help a surgeon plan and design the sinus guide. It also provides an convenient way to test a surgical guide by comparison to a 3D printed model of a patient's maxilla or to a patient's maxilla and to easily modify the design and improve its fit and prevent instability prior to production of a surgical guide to be used in a surgical procedure.

The thickness of the guide may taper down around the outline of the surgical window provided by the guide, for example, at a <15, 15, 20, 30, 40, 45, 50, 60 or >60° angle so that the supporting portions of the guide which fit over maxillary bone are thicker than the edge of the surgical window that forms the circumference of the surgical window. The portion of the guide that provides an outline of a surgical window is smooth without notches or other imperfections, such as those which can be produced by heating that would impede the marking of the surgical window on the maxilla of the patient.

When the guide in this invention is fabricated for edentulous patients who have no teeth it gains support only from the interior maxillary ridge and lateral wall as shown in FIG. 5. The guide does not need to rest on the lower jaw.

A surgical guide as disclosed herein may have a wall thickness ranging from 1.5, 2, 3, 4, 5, to >5 mm; be offset from bone and surrounding dental structures by about 0.05, 0.06, 0.07, 0.08, 0.09, 0.1 to >0.1 mm, This guide is trial fit on a 3D printed model as a way to assure a close fit with little or no offset. In cases where undesirable bone undercut is present The surfaces of the guide that are supported by bone are smooth and closely fit the supporting portions of the maxilla and provide a stable, non-rocking, and comfortable fit. These surfaces are designed to conform and closely fit to the maxilla and thus are concave where the maxilla is convex, such as around the surgical window, and concave where the maxilla is convex, for example, around the gum line. The guide also fits securely to the alveolar margin or inferior ridge of the maxilla.

The surface of the guide is smoother and reduces friction and marker or instrument "hang up" as the surgeon along the outline of the guide compared to conventionally cast guides produced without stereo lithography 3D printing. In some embodiments, the acrylic resin used to make the guide may contain or be coated with a second material, such as PTFE (Teflon®) to facilitate movement of markers and surgical instruments around the guide, especially portions around the circumference of the opening defining the surgical window.

The invention provides precise, stable and more accurate surgical guide. In some embodiments, both a model of a patient's maxilla and a model of the surgical guide may be printed at 1.0, >1.0, 1.1, 1.2, 1.3, 1.4, 1.5, 1.6, 1.7, 1.8, 1.9, 2.0 or >2.0 scale to enhance visualization and evaluation of the fit between the guide and a patient's maxilla.

In preferred embodiments, the guide has a smooth surface both in contact with the patient's maxillary and surrounding areas, around a surgical window and other surfaces that come into contact with a surgeon's tools during a sinus graft or other procedure for which the guide is used. These smooth surfaces prevent "hang up" of dental tools during a procedure rendering it easier and safer than procedures using guides with rougher surfaces.

In other embodiments, the surgical guide will have tapered edges around the window or around portions fitting on boney structures so as to more easily fit the patient's maxilla and surrounding structures. The primary use of the guide described herein is for sinus grafting.

The terms "subject" and "patient" unless otherwise indicated, are used synonymously to refer to individuals in need of a surgical procedures using the surgical guides disclosed herein. A patient may be female or male, young or old, preferably, a person having at least one, preferably all, permanent teeth erupted, such as someone that is <10, 10, 11, 12, 13, 14, 15, 16, 17, 18, 90, 20, 25, 30, 35, 40, 45, 50, 55, 60, 65, 70, 75, 80, 85, 90 or >90 years old. A subject may have or be at risk of periodontal disease, further loss of teeth or resorption of bone in the maxilla and jaw. Some subjects may have lost one or more permanent teeth, such as one or more molars, canine teeth, or incisors, for example, 1, 2, 3, 4, 5, 6, 7, 8, 9, 10, 11, 12, 13, 14, 15, 16, or more teeth, from the upper and/or lower arches, for instance, a subject may have lost 1, 2, 3, 4, 5, or 6 six maxillary molars. A subject may seek to undergo surgery on the maxilla to support one or more tooth implants for improved appearance, improved speech, improved comfort, better oral health such as to avoid periodontal disease or bone resorption around the teeth, or to provide permanent, durable teeth in place of dentures.

Cone-beam computed tomography. Cone-beam computed tomography systems (CBCT) are a variation of traditional computed tomography (CT) systems. The CBCT systems used by dental professionals rotate around the patient, capturing data using a cone-shaped X-ray beam. These data are used to reconstruct a three-dimensional (3D) image of the following regions of the patient's anatomy: dental (teeth); oral and maxillofacial region (mouth, jaw, and neck); and ears, nose, and throat ("ENT"). Further description of cone-beam computed tomography, CBCT devices, cone-beam reconstruction algorithms, and 3D imaging methods such as filtered back projection and iterative reconstruction are incorporated by reference to https://_en.wikipedia.org/wiki/Cone_beam_computed_tomography; and to https://_www.fda.gov/Radiation-EmittingProducts/RadiationEmittingProductsandProcedures/MedicalImaging/MedicalXRays/ucm315011.htm (each last accessed Feb. 21, 2019).

FDA tracked dental 3D printer resins and surgical guide resins useful for printing models, prototypes, or surgical guides, are commercially available and include all those described by https://_www.microndental.com/regulatory/fda-approved-cleared-3d-printer-resins (last accessed Feb. 21, 2019, incorporated by reference). Examples of surgical guide resins include those of class 1, NDP such as VarseoWax Surgical Guide® available at https://_www.bego.com/index.php?id=1884&L=994 or https://_usa.bego.com/fileadminBEGO-USA/user_download s/MediaLibrary/Conventional-Solutions/Materials/VarseoWax-SurgicalGuide/de_41032_sb_EN.pdf (each last accessed Feb. 21, 2019, incorporated by reference). FDA tracked 3D printable resins include Befo (9611514) VarseoWax surgical guide, class 1-NDP; and Vertex E-Guide Tint; NextDent SG (504122); EnvisionTec EGuard (516947); Structo (3014329597) Structomer Guide (563712); and Dreve FotoDent Guide; Multiple (459759).

A preferred 3D ink/resin used for the invention is Dental SG. The links below describe FDA approved materials and are each incorporated by reference.
https://_formlabs.com/media/upload/DentalSG-DataSheet.pdf or generally at
https://_formlabs.com (last accessed Mar. 28, 2019)
https://_www.goprint3d.co.uk/blog/breaking-formlabs-announce-dental-sg-resin/(last accessed Mar. 28, 2019)

3D printers. Any type of 3D printer that can print a dental guide as disclosed herein using the types of 3D printing inks disclosed herein may be used to produce a model, porotype or actual surgical guide 3D printer manufacturers include those listed at https://_en.wikipedia.org/wiki/List_of_3D_printer_manufacturers (last accessed Feb. 21, 2019, incorporated by reference). A variety of different dental 3D printers are available and are incorporated by reference to Formlabs white paper, Introduction to digital dentistry and 3D printer buyer's guide, January, 2018 (accessed online Feb. 21, 2019; incorporated by reference).

Any suitable 3D printer or 3D ink/resin may be used to make the surgical guide of the invention. In some embodiments the printer is a Formlabs2 or Formlabs Form 2 printer and the ink/resin used is Dental SG. FDA approved materials are also described by the links above.

Example

A CBCT scan of a patient's maxilla and jaw is taken using a VGi Evo instrument (https://_www.cefladental.com/our-brands/newtom/, last accessed Mar. 5, 2019, incorporated by reference) to diagnose and plan treatment of an edentulous patient. The CBCT cross section is used to evaluate and plan sinus grafting to support a dental implant. Data from the scan is provided in a DICOM file which can be used to provide a 3D model of the maxillary bone.

DICOM reconstruction software (InVesalius 3.0) is used to transform that DICOM data set from the CBCT scan into a 3D bone model. The bone model is exported as an STL file.

The STL file depicting maxillary bone is superimposed on the CBCT data using implant-planning software (BlueSky Plan; https://_blueskybio.com/pages/blue-sky-plan-guided-surgery-software, last accessed Mar. 5, 2019, incorporated by reference). Implant position is selected and a gum-bone supported surgical guide is designed which includes the implant position and which covers the lateral wall of the sinus and zygomatic process of the maxilla.

Using a cut tool an outline of the proposed lateral window with proper extension is produced. The outline is cut through the gum/bone model and the surgical guide. The surgical guide design is exported as an STL file.

The surgical guide STL file is imported into design software (Meshmixer; http://_www.meshmixer.com/; last accessed Mar. 5, 2019, incorporated by reference) in order to contour the smooth the surgical guide.

The design of the guide is then exported as an STL file into 3D printing software (PreForm; last accessed Mar. 5, 2019, incorporated by reference) and printed in FDA approved acrylic resin.

A prototype surgical guide is produced and fitted to a 3D print of the patient's maxillary jaw. The fit of the surgical guide is evaluated and the design of the surgical guide is modified to more closely fit the gum or bone of the patient and to provide a surgical window above the sinus. After evaluation of the fit, the design is modified if necessary and a revised, close-fitting surgical guide is 3D printed.

Midcrestal, sucular and vertical releasing incisions are made and a full-thickness mucopariosteal flap is exposed on the lateral wall of the maxillary sinus. The 3D printed guide is placed intraorally. After guide fit confirmation, a marker (surgical pencil) is used to outline of a lateral window is traced and an osteotomy is produced using a #8 surgical bur or osteotomy instrumentation like DASK drills. The sinus membrane is reflected and elevated.

A mixture of allograft and autologous graft material is placed in the sinus. A collagen membrane (Bioglide, Geistlich Pharma Inc.) is placed over the lateral window and secured with 2 tacks. The flap is reapproximated and sutured with a passive primary closure using polytetrafluorethylene (Gortex, W1>Gore & Associates) and chromic gut (Ethicon US, LLC). A post-operative CBCT is performed to evaluate the sinus graft.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a patient missing one or more teeth, comprising:
   placing a 3D printed bone supported maxillary sinus surgical guide in the mouth of the patient thereby marking access to the sinus, then
   installing a dental implant in the mouth of the patient;
   wherein prior to the placement of the 3D printed bone supported sinus surgical guide in the mouth of the patient, the method further comprises:
      making the 3D printed bone supported maxillary sinus surgical guide by:
      obtaining an STL file describing a maxillary bone structure of the patient as imaged by cone beam computerized tomography ("CBCT");
      producing an STL file describing the 3D printed bone-supported maxillary sinus surgical guide using implant planning software and the STL file describing the maxillary bone structure of the patient;
      3D printing the 3D printed bone-supported maxillary sinus surgical guide from a UV curable resin using the STL file describing the 3D printed bone-supported maxillary sinus surgical guide, and curing the UV curable resin with light;
      3D printing a scale model that comprises maxillary surfaces in contact with the 3D printed bone-supported maxillary sinus surgical guide from a UV curable resin using the STL file describing the maxillary bone structure of the patient, and curing the UV curable resin with light; and
      test fitting the 3D printed bone-supported maxillary sinus surgical guide to the scale model.

2. The method of claim 1, wherein the UV curable resin is cured without heat curing.

3. The method of claim 1, wherein obtaining the STL file describing the maxillary bone structure of the patient comprises transforming data in a digital imaging and communications in medicine (DICOM) file into an STL file using DICOM reconstruction software.

4. The method of claim 1, further comprising performing a CBCT scan of the maxillary bone structure of the patient.

5. The method of claim 1, wherein producing the STL file describing the bone-supported maxillary sinus surgical guide comprises determining a position of a window that covers a lateral wall of the sinus and zygomatic process of the maxilla.

6. The method of claim 1, wherein producing the STL file describing the bone-supported maxillary sinus surgical guide comprises determining a tooth implant position.

7. The method of claim 1, wherein producing the STL file describing the bone-supported maxillary sinus surgical guide comprises contouring and/or smoothing the design of the bone-supported maxillary sinus surgical guide.

8. The method of claim 1, further comprising surgically forming a lateral sinus window using the 3D printed bone-supported maxillary sinus surgical guide.

9. The method of claim 1, further comprising performing a sinus lift or sinus augmentation using the 3D printed bone-supported maxillary sinus surgical guide.

10. The method of claim 1, wherein the patient is edentulous.

* * * * *